US011844544B2

(12) United States Patent
Kern

(10) Patent No.: US 11,844,544 B2
(45) Date of Patent: Dec. 19, 2023

(54) IRRIGATION DEVICES IN DEBRIDEMENT SYSTEMS

(71) Applicant: Medtronic PS Medical, Inc., Louisville, CO (US)

(72) Inventor: Andrew Kern, Longmont, CO (US)

(73) Assignee: Medtronic PS Medical, Inc., Louisville, CO (US)

( * ) Notice: Subject to any disclaimer, the term of this patent is extended or adjusted under 35 U.S.C. 154(b) by 302 days.

(21) Appl. No.: 17/411,182

(22) Filed: Aug. 25, 2021

(65) Prior Publication Data

US 2023/0067743 A1 Mar. 2, 2023

(51) Int. Cl.
*A61B 17/32* (2006.01)
*A61B 17/00* (2006.01)

(52) U.S. Cl.
CPC .......... *A61B 17/32002* (2013.01); *A61B 2017/00199* (2013.01); *A61B 2017/00473* (2013.01); *A61B 2017/320004* (2013.01); *A61B 2017/320024* (2013.01); *A61B 2017/320032* (2013.01); *A61B 2017/320064* (2013.01); *A61B 2217/005* (2013.01); *A61B 2217/007* (2013.01)

(58) Field of Classification Search
CPC .... A61B 17/32002; A61B 2017/00199; A61B 2017/00473; A61B 2017/320004; A61B 2017/320024; A61B 2017/320064; A61B 2017/320032; A61B 2217/005
See application file for complete search history.

(56) References Cited

U.S. PATENT DOCUMENTS

| | | |
|---|---|---|
| 5,091,656 A | 2/1992 | Gahn |
| 5,484,402 A | 1/1996 | Saravia et al. |
| 5,569,178 A * | 10/1996 | Henley .......... A61B 17/320783 604/22 |
| 5,573,515 A | 11/1996 | Wilson et al. |
| 5,669,876 A | 9/1997 | Schechter et al. |
| 5,685,821 A | 11/1997 | Pike |
| 5,800,383 A | 9/1998 | Chandler et al. |
| 5,810,765 A | 9/1998 | Oda |
| 5,882,339 A | 3/1999 | Beiser et al. |
| 5,931,808 A | 8/1999 | Pike |
| 6,086,598 A | 7/2000 | Appelbaum et al. |
| 6,162,194 A | 12/2000 | Shipp |
| 6,269,340 B1 | 7/2001 | Ford et al. |

(Continued)

*Primary Examiner* — Sarah A Long
(74) *Attorney, Agent, or Firm* — Carter, DeLuca & Farrell LLP

(57) ABSTRACT

A device for use with a debridement system is disclosed. The device includes an outer tubular shaft having an inner surface defining a lumen along an axis, the inner surface having an inner surface diameter. An inner tubular shaft is disposed within the lumen and rotatable within the outer tubular shaft. The inner tubular shaft includes an outer surface having an outer surface diameter less than the inner surface diameter. The inner surface of the outer tubular shaft with the outer surface of the inner tubular shaft forms a channel along the axis to receive fluid from the fluid source. The rotor is disposed in the channel and includes an axially extending helicoid blade coupled to the inner tubular shaft. The blade rotates within and with respect to the outer tubular shaft and exerts an axial thrust on the fluid in the channel with respect to the outer tubular shaft.

20 Claims, 2 Drawing Sheets

(56) References Cited

U.S. PATENT DOCUMENTS

| | | |
|---|---|---|
| 6,780,166 B2 | 8/2004 | Kanda et al. |
| 6,899,697 B2 | 5/2005 | Fowler et al. |
| 7,150,713 B2 | 12/2006 | Shener et al. |
| 7,678,070 B2 | 3/2010 | Kumar et al. |
| 7,857,784 B2 | 12/2010 | Schmidberger |
| 8,597,261 B2 | 12/2013 | Knapp |
| 8,915,842 B2 | 12/2014 | Weisenburgh, II et al. |
| 9,332,894 B2 | 5/2016 | Cheng et al. |
| 9,345,386 B1 | 5/2016 | Cheng |
| 9,585,547 B2 | 3/2017 | Cheng et al. |
| 10,022,040 B2 | 7/2018 | Cheng et al. |
| 10,028,644 B2 | 7/2018 | Konstorum et al. |
| 10,369,267 B2 | 8/2019 | Norman et al. |
| 10,588,493 B2 | 3/2020 | Elia et al. |
| 10,631,717 B2 | 4/2020 | Cheng et al. |
| 11,266,303 B2 | 3/2022 | Konstorum et al. |
| 11,311,338 B2 | 4/2022 | Fan et al. |
| 2003/0212379 A1 | 11/2003 | Bylund et al. |
| 2004/0202561 A1* | 10/2004 | Hershberger ....... F04B 43/1253 |
| | | 417/477.7 |
| 2005/0209621 A1 | 9/2005 | Gordon et al. |
| 2006/0064053 A1 | 3/2006 | Bollish et al. |
| 2007/0078370 A1 | 4/2007 | Shener et al. |
| 2007/0233003 A1 | 10/2007 | Radgowski et al. |
| 2008/0154184 A1 | 6/2008 | Blight et al. |
| 2008/0281343 A1* | 11/2008 | Dewey ............... A61B 17/1675 |
| | | 606/180 |

\* cited by examiner

IRRIGATION DEVICES IN DEBRIDEMENT SYSTEMS

BACKGROUND

The present disclosure relates generally to methods, and apparatuses, and systems that allow for fluid irrigation of tissues with debrider systems, which includes microdebrider systems, with such debrider systems that can provide for cutting of bone, cartilage, and soft tissue. Debrider systems can be particularly suitable for sinus applications and nasopharyngeal/laryngeal procedures.

Debrider systems may be suitable for a variety of procedures including ear, nose and throat (ENT) procedures, head and neck procedures, otology procedures, including otoneurologic procedures. Debrider systems may be suitable for a variety of other surgical procedures including mastoidectomies and mastoidotomies; nasopharyngeal and laryngeal procedures such as tonsillectomies, trachael procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and transsphenoidal procedures; rhinoplasty and removal of fatty tissue in the maxillary and mandibular regions of the face, as well as other procedures. Such procedures are typically challenging due to the location to sensitive organs such as the eyes and brain, the relatively small size of the anatomy of interest to the surgeon, and the complexity of the typical procedures.

Debrider systems present devices for powered tissue cutting, sealing, and removal during sinus surgery. In one example, a microdebrider includes a rotary powered handpiece, which may be manipulated by a clinician. The handpiece that may be coupleable to a one of a portfolio of application-specific, anatomic-specific, sharp mechanical cutting components such as rotatable blades or burs. The portfolio may include a set of different debrider devices that interface with the patient and can apply a suitable treatment. In some examples, the debridement devices are single use and can be appropriately disposed of subsequent to surgery. The handpiece may also be coupled to a console for driving the microdebrider, and to provide a source of fluid or suction. An example fluid may include saline or saline with a medicament, and can be presented to the handpiece and, ultimately, to the tissue site via a pump applied to the source fluid. In some examples, the mechanical cutting components can be rotated at speeds of up to thirty-thousand rotations per minute, and the distal ends of the mechanical cutting components also can provide for tissue irrigation with fluid and suction for rapid tissue removal. In some examples, the debrider systems can be used to apply radiofrequency energy with saline irrigation for cutting, ablating, or coagulating tissue. Debrider systems are particularly successful for powered tissue cutting and removal during sinus surgery.

Endoscopic sinus irrigation devices are separate devices from debrider systems and provide for pressurized sinus irrigation to help remove bacteria that cause ongoing sinus infections such as chronic sinusitis. Such irrigation devices include a manipulatable handpiece coupled to a fluid source and to an irrigation channel having a distal nozzle to deliver the fluid to tissue. In one example, the handpiece can deliver a rotating spray of pressurized saline at 5 mL/second to the nozzel, enabling access to the sinuses for direct sinus irrigation and fluid removal. Again, the fluid can be presented to the handpiece and, ultimately, to the tissue site via a pump applied to the source of fluid. Functional endoscopic sinus surgery (FESS) with such irrigation devices is a minimally invasive surgical procedure used to treat chronic rhinosinusitis, an infection of the sinuses. FESS opens up sinus air cells and sinus ostia (openings) with an instrument aided by an endoscope. The use of FESS as a sinus surgical method has now become widely accepted.

SUMMARY

To summarize the current techniques of various ENT procedures such as sinus procedures can employ debridement systems with rotatable blades or burs. Clinicians may select an appropriately configured blade or bur based on the application. In some examples, the debridement systems may provide suction, such as a negative pressure from a tubular section of the tip of the blade or bur, and irrigation or lavage or for tissue sealing or ablation, such as with a relatively low pressure fluid from a port near the blade or bur. In procedures that involve the removal of bacteria in sinus infections, relatively higher pressure fluid or irrigation can be provided with an endoscopic irrigation system that is separate and distinct from the debridement system.

The present disclosure is directed to a system and devices that provides for more flexible and treatment options to a clinician during surgery with the debridement system. For example, a surgeon may incorporate the use of relatively high pressure fluid or irrigation with an attachment in the portfolio of debridement devices compatible for use with the debridement system rather than with a separate purpose-built system. The system and devices implement the techniques of driving rotation of an inner tubular shaft with respect to an outer tubular shaft to power a distal device to fluid pump that interfaces with the patient. The fluid pump debrider device can be incorporated into a portfolio of blades, burs, and other debrider device that, in one example, may be exchanged as determined appropriate in a debrider system.

In a first aspect, the present disclosure is directed to a debridement system having a handpiece operatively coupled to and driven by a power console and coupled to a source of fluid. The handpiece receives the fluid from the source of fluid. An irrigation is coupled to the handpiece and receives the fluid from the handpiece. The irrigation device includes an outer tubular shaft, an inner tubular shaft, and a rotor. The outer tubular shaft includes a distal end, a proximal end, and an inner surface defining a lumen along an axis, the inner surface having an inner surface diameter. The inner tubular shaft is disposed within the lumen and rotatable within the outer tubular shaft. The inner tubular shaft includes an outer surface that include an outer surface diameter that is less than the inner surface diameter of the outer tubular shaft. The inner surface of the outer tubular shaft, together with the outer surface of the inner tubular shaft, form a channel along the axis, and the channel is configured to receive fluid from the fluid source. The rotor is disposed in the channel and includes an axially extending helicoid blade coupled to the inner tubular shaft, such as to the outer surface of the inner tubular shaft. The helicoid blade rotates within and with respect to the outer tubular shaft and exerts an axial thrust on the fluid in the channel with respect to the outer tubular shaft.

In another aspect, the present disclosure is directed to a device for use with a debridement system coupled to a fluid source. The device includes an outer tubular shaft, an inner tubular shaft, and a rotor. The outer tubular shaft includes a distal end, a proximal end, and an inner surface defining a lumen along an axis, the inner surface having an inner surface diameter. The inner tubular shaft is disposed within the lumen and rotatable within the outer tubular shaft. The inner tubular shaft includes an outer surface that include an outer surface diameter that is less than the inner surface diameter of the outer tubular shaft. The inner surface of the outer tubular shaft, together with the outer surface of the inner tubular shaft, form a channel along the axis, and the channel is configured to receive fluid from the fluid source. The rotor is disposed in the channel and includes an axially extending helicoid blade coupled to the inner tubular shaft, such as to the outer surface of the inner tubular shaft. The helicoid blade rotates within and with respect to the outer tubular shaft and exerts an axial thrust on the fluid in the channel with respect to the outer tubular shaft.

The present disclosure is directed to examples of rotatable debridement devices that can provide pressurized irrigation and lavage via an attachment to a handpiece also applied to cut and remove tissue via surgery. The rotatable debridement devices can be included in a portfolio of attachable tools to the handpiece and selectable by a surgeon to provide functionality and features in therapy previously unavailable in the tools of the debridement systems. For example, a surgeon working with multiple tools to provide therapy can apply a single debridement system rather than substitute the debridement system with an endoscopic irrigation system for therapy delivery.

The features of the debridement systems and rotatable debridement devices of the present disclosure are described with reference to particular procedures such as sinus surgery for illustration only. The debridement systems and rotatable debridement devices of the present disclosure can be configured and applied to as well as useful for other purposes, and other purposes can include other locations of a patient.

DETAILED DESCRIPTION

Figure 1:
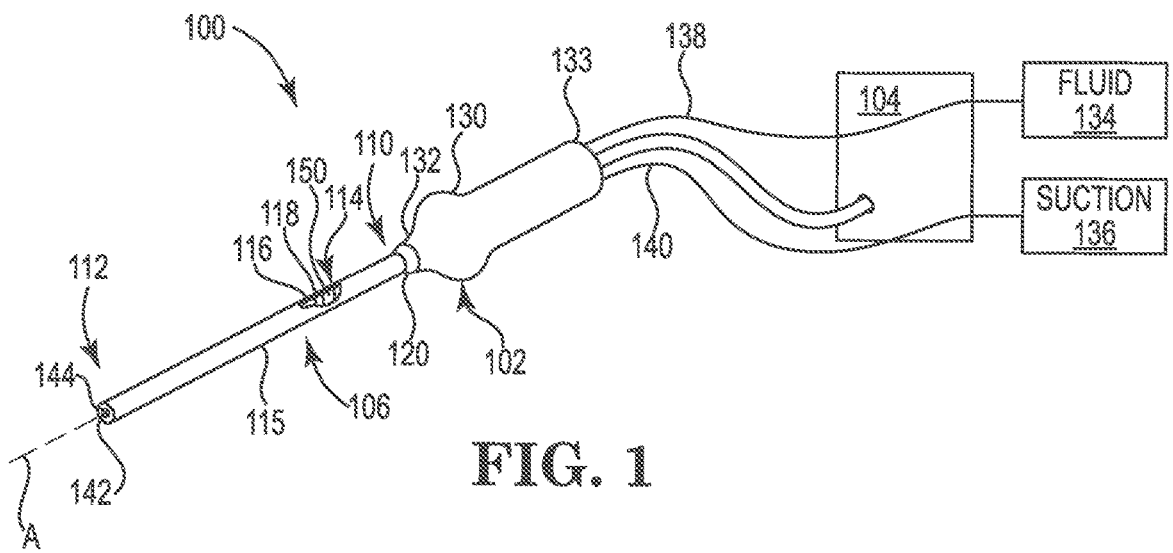
FIG. 1 is a schematic perspective view illustrating an example medical system such as an example debridement system with a partially cutaway rotatable debridement device or the present disclosure, such as a rotatable irrigation device.

FIG. 1 illustrates an example debrider system 100. The debrider system 100 of the example includes a handpiece 102, such as a microdebrider handpiece, which can be manipulated by a user such as a clinician or surgeon to control a rotatory motor. The handpiece 102 is coupled to and driven by a power console that includes a rotary motor, such as an integrated power console (IPC) 104. A rotatable debridement device 106 is attached to the handpiece 102 that can interface with tissue and effect treatment. In one example, the rotatable debridement device 106 is removably attached to the handpiece 102.

The rotatable debridement device 106 includes a proximal end region 110, a distal end region 112, and a plurality of tubular shafts 114 disposed along an axis A having longitudinal sides 115 extending along the axis A from the end regions 110, 112. The plurality of tubular shafts 114 include an outer tubular shaft 116 and an inner tubular shaft 118 disposed within the inner tubular shaft 116. The inner tubular shaft 118 is coaxially maintained within a lumen of the outer tubular shaft 116, and the inner tubular shaft 118 can be rotated about axis A within the lumen with respect to the outer tubular shaft 116. In some examples, the plurality of tubular shafts 114 can include additional shafts. The tubular shafts 116, 118 can be constructed from a unitary piece of material, axial segments of the material, or axial segments of dissimilar materials. Other combinations are contemplated. The tubular shafts 116, 118 are presented with straight tubes, i.e., shafts of constant diameter, for illustration only. Some examples may include sections with diverse diameters or conical shapes. The rotatable debridement device 106 can include an interface 120 that facilitates removable coupling to the handpiece 102.

The illustrated handpiece 102 includes a housing 130 having a distal section 132 operably coupled to the rotatable debridement device 106, such as to the interface 120, and a proximal section 133 operably coupled to the IPC 104. In one example, the handpiece 102 includes a hub (not shown) carried within the housing 130 and operably coupled to the inner tubular shaft 118. The hub is rotatable with respect to the housing 130. The hub in the example is configured to be manipulated by a user, such as a clinician, to rotate the inner tubular shaft 118 with respect to the outer tubular shaft 116.

The IPC 104 is operably coupled to the hub and is configured to drive selective rotation of the inner tubular shaft 118 about the axis A within and with respect to the outer tubular shaft 116. For instance, the user is able control rotation and rotation speed of the inner tubular shaft 118 with respect to the outer tubular shaft 116 via the IPC. For example, IPC may drive the inner tubular shaft at a constant speed, such as speed as measured by revolutions per minute, at various speeds, or may permit a user to vary the speeds during operation. Operation of the debridement system 100 can include driving the inner tubular member 118 or not driving the inner tubular member 118. A user selects whether to operate the rotatable debridement device 106 at the constant speed. In another example, the IPC may drive the inner tubular member 118 at various speeds, such as selected speeds from slow to tens of thousands of revolutions per minute. The user may select one of many speeds to operate the rotatable debridement device 106 including varying the speed of the rotatable debridement device 106 during operation.

The IPC 104 is also coupled to a fluid source 134, such as a liquid, and may also be operably coupled to a suction source (such as a source of negative pressure) 136. (The IPC 104 is presented for illustration. In some examples of system 100, however, a fluid source 134 and suction source 136 does not interface with the IPC.) The IPC 104, in one example, may be programmed to selectively provide fluid and suction to the handpiece 102. A fluid source connector 138 and a suction source connector 140 are provided between the IPC 104 and the handpiece 102 and in fluid communication with the fluid source 134 to provide fluid to the handpiece 102 and in fluid communication to the suction source 136 to provide suction to the handpiece 102, respectively. Fluid in fluid source 134 may include a saline solution such as saline and a medicant. Suction and fluid are provided along the rotatable debridement device 106 to the distal end region 112. For example, fluid is provided from the handpiece 102 along a channel formed between the outer tubular shaft 116 inner tubular shaft 118 to the distal end region 112. The channel is configured to be in fluid communication with the fluid source 134. Suction may be provided from a lumen within the inner tubular shaft 118 via suction source connector 140, and the lumen is in fluid communication with the suction source 136 via fluid source connector 138. The debrider system 100 may further include a fluid pump (not shown), such as peristaltic pump, disposed between the fluid source 134 and the handpiece 102, such as disposed between the fluid source 134 and the IPC 104 to force fluid to the handpiece 102 via a mechanism other than gravity.

In the rotatable debridement device 106, the channel for the fluid is terminated at the distal end region 112 via a fluid port 142 that may be configured in the form of a nozzle. The nozzle may be bendable or configurable by the user to direct the outflow of fluid from the rotatable debridement device 106 in a selected direction. In some examples, the rotatable debridement device 106 may include other features at the distal end region such as a debridement tools, which can include blades and burs, in addition to the fluid port 142. The lumen in the inner tubular shaft 118 can be terminated via a suction port 144.

The rotatable debridement device 106 includes a rotor 150 disposed within the channel and coupled to the outer tubular shaft 116 or inner tubular shaft 118 and configured to be driven via the handpiece to rotate about axis A. For instance, the rotor 150 may be coupled to an outer surface of the inner tubular shaft 118 to rotate with the inner tubular shaft 118 and with respect to the outer tubular shaft 116. In this example, the rotor 150 exerts an axial thrust on the fluid in the channel with respect to the outer tubular shaft 116 when the inner tubular shaft is rotated or driven by the IPC to direct the fluid via force to the fluid port 142. In this respect, the axial thrust on the fluid is greater than and in addition to the force on the fluid provided via the pump and gravity and other mechanisms disposed between the fluid source 134 and the handpiece 102. In one example, the rotor 150 includes an axially extending helicoid blade coupled to the inner tubular shaft 118, such as to an outer surface of the inner tubular shaft 118, to rotate with the inner tubular shaft 118 and with respect to the outer tubular shaft 116. For instance, the helicoid blade can be formed via splines attached to the outer surface of the inner tubular shaft 118 or via cuts to the outer surface of the inner tubular shaft 118, such as etching or knurling.

In one example, the debridement system 100 includes the rotatable debridement device 106 configured as an axial pump for a fluid source 134. For instance, the rotatable debridement device 106 can be a releasably attachable or disposable device for use as an axial pump during procedures. As an example, the rotatable debridement device 106 configured as an axial pump can increase pressure of the fluid, such as irrigation fluid to provide irrigation and lavage during sinus surgery. In one example, the rotatable debridement device 106 can include a bur or blade or used to replace a bur or blade attached to the handpiece 102 to provide powered tissue cutting and removal as well as pressurized irrigation via a debrider system such as debrider system 100 rather than via multiple systems in an operating room or clinician office such as a debrider system and an endoscopic irrigation system.

A user may operate a switch, such as a mechanism on the handpiece or a footswitch, operably coupled to the IPC, to manipulate rotation of the inner tubular member and the speed of rotation of the rotor to selectively apply thrust to the fluid and the speed or pressure of the fluid emanating from the fluid port 142. In example of the debridement system 100 in which the user may vary speed of rotation, speed of the rotation of the rotor 150 may be related to the force or thrust of the fluid from the fluid port 142, e.g., a faster selected speed of rotation may result in greater force or thrust of the fluid than a slower selected speed of the rotation. In some examples, operation of the switch activates both the fluid pump to supply fluid to the rotatable debridement device 106 and the rotor 150 to accelerate the fluid through the fluid port 142. The user may further operate another mechanism to selectively apply a suction from the suction port 144 of the rotatable debridement device 106. In some examples, activation of the rotor 150 is independent of application of the suction.

Figure 2:
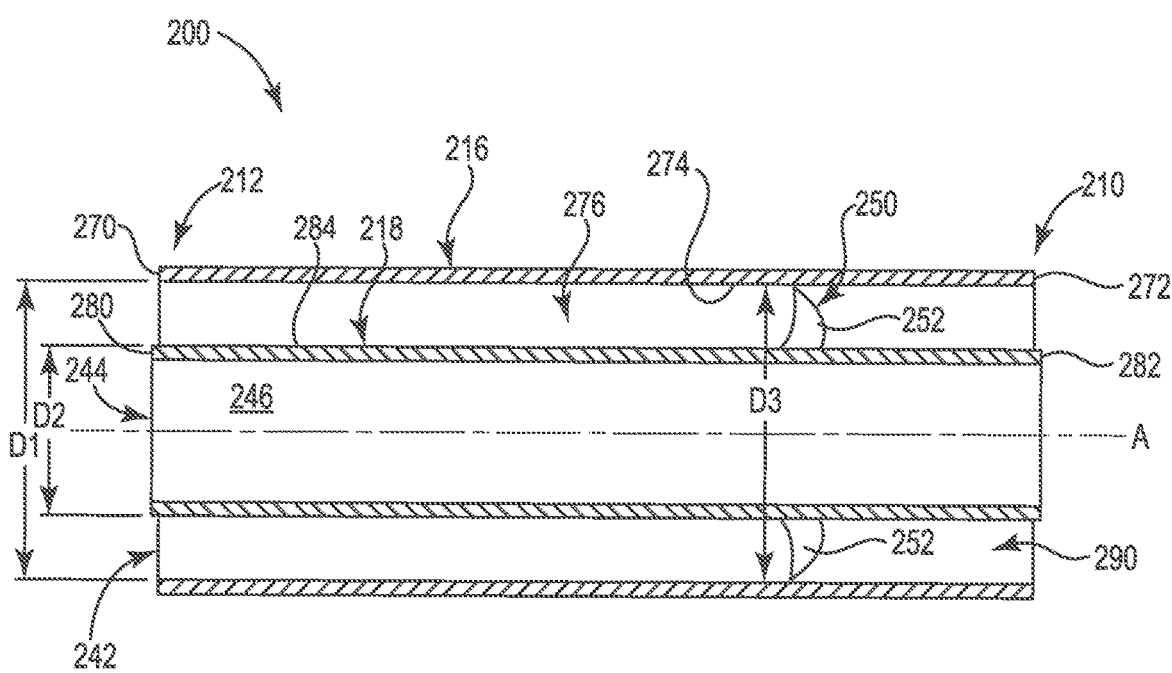
FIG. 2 is sectioned side schematic view illustrating an example debridement device such a rotatable debridement device of the debridement system of FIG. 1.

FIG. 2 illustrates an example device 200 for use with a debridement system coupled to a fluid source, for example, device 200 can be an implementation of rotatable debridement device 106. The device 200 includes an outer tubular shaft 216, and inner tubular shaft 218, and a rotor 250. The device 200 can include a proximal end region 210, a distal end region 212, and a longitudinal portion 215 extending along axis A between the proximal end region 210 and the distal end region 212. In one implementation, the proximal end region 210 of device 200 is suitable for coupling to a handpiece of the system, such as handpiece 102, and the distal end region of the device 200 is suitable for interfacing with the patient to effect treatment. The outer tubular shaft 216 includes a distal end 270, a proximal end 272, and an inner surface 274 defining a lumen 276 along an axis A, the inner surface 274 having an inner surface diameter D1. The inner tubular shaft 218 is disposed within the lumen 276 and rotatable about axis A within the outer tubular shaft 216. The inner tubular shaft 218 includes a distal end 280, a proximal end 282, and an outer surface 284 that include an outer surface diameter D2 that is less than the inner surface diameter D1 of the outer tubular shaft 216 (D1>D2). The inner surface 274 of the outer tubular shaft 216 is spaced-apart from the outer surface 284 of the inner tubular shaft 218. The inner surface 274 of the outer tubular shaft 216, together with the outer surface 284 of the inner tubular shaft 218, form a channel 290 along the axis A, and the channel 290 is configured to receive fluid from the fluid source, such as fluid source 134. For instance, when the device 200 is installed in a debrider system, such as releasably coupled to the debrider system at the proximal end, the channel 290 is in fluid communication with the fluid source such as via fluid connectors to the handpiece or the IPC.

Diameters illustrated in the disclosure are presented with reference to straight tubes for discussion only. In examples with tubular shafts with multiple or varying diameters, as well as for straight tubes, the measurements of the diameters regarding the relation of the inner surface to the outer surface, and the inner surface to components of the rotor or the outer surface to the components of the rotor are taken at the same axial location.

The rotor 250 is disposed in the channel 290 and includes an axially extending helicoid blade 252 coupled to the inner tubular shaft 218, such as to the outer surface 284 of the inner tubular shaft 218. The rotor 250 and helicoid blade 252 are schematically illustrated in FIG. 2. The helicoid blade 252 rotates within and with respect to the outer tubular shaft 216 and exerts an axial thrust on the fluid in the channel with respect to the outer tubular shaft 216. In one example of a rotor 250, the blade 252 is attached to the inner tubular shaft 218 such as splines attached to the inner tubular shaft 216. In another example, the blade 252 can be integrally formed with the inner tubular shaft 216, such as the blade is formed out the material of the inner tubular shaft. In still another example, the rotor 250 can be formed to be an axial section of the inner tubular shaft. For instance, the rotor 250 include an outer surface having a diameter substantially the same as the inner surface diameter of the outer tubular shaft 216, and the rotor includes an inner surface forming a lumen. The rotor can include an axial distal end and a proximal end, that can be attached to the end or ends of the tubular shafts to form the inner tubular shaft 216.

In one example, the proximal end region 210 is configured to interface with and couple to a handpiece of a debrider system, such as handpiece 102 of system 100. In one example, the proximal end region 210 is releasably couple-able to the handpiece, such that the device can be attached to and removed from the handpiece during surgery. In one example, the device 200 can be repeatedly attached to and removed from the handpiece, such as if a clinician returns to use the device 200 after another debrider device in the portfolio. The proximal end 282 of the inner tubular shaft 218 can interface with a hub of the handpiece such that the IPC can rotate the inner tubular shaft 218 about axis A with respect to the outer tubular shaft 216. In some examples, device 200 can be configured to allow the inner tubular shaft 218 to rotate with respect to the outer tubular shaft 216 at speeds of tens of thousands of revolutions per minute. The outer tubular shaft 216 interfaces with handpiece in a manner to configure fluid communication with a fluid source and the channel 290 defined between the inner surface 274 of the outer tubular shaft 216 and the outer surface 284 of the inner tubular shaft 218. For example, the channel 290 can be in fluid communication with the fluid connector 138 of FIG. 1.

The rotor 250 can be characterized as an impeller or propeller disposed in the channel 290 and attached to rote with the rotatable tubular shaft, such as the inner tubular shaft 218. The rotor 250 includes a helicoid blade 252 defined by a root, tip, and pitch as in the case of a propeller. The helicoid blade 252 can include a plurality of helicoid blades, such as a plurality of helicoid blades radially spaced apart around a circumference of the rotatable tubular shaft. The root of the blade 252 is attached to the rotatable tubular shaft, and the tip is an edge included on the blade 252 at the further point from the root. The blade 252 may extend across the channel 290 radially from the outer surface 284 of the inner tubular shaft 218 to the inner surface 274 of the outer tubular shaft 216. If the rotor 250 is configured to form an axial segment of the inner tubular shaft 218 with adjacent segments, the rotor can further define an axial hub having a lumen in which the blade is attached to the hub of the rotor, or rotor hub. In one example, the diameter of the blade 252, or rotor 250, at the tip D3 is about equal to or less than the inner surface diameter D1 of the outer tubular shaft 216 (D1≥D3>D2) The blade 252 may include a distal face toward the distal end region 210 and a proximal face toward the proximal end region 212. A nominal pitch is an axial distance of a rotation of the blade 252. In some examples, the blade 252 may extend axially for at least a full rotation, but, in other examples, a plurality of blades that do not extend axially for a full rotation and include a face that does not extend radially for a full circumference of the rotatable tubular shaft may be radially spaced-apart at location on a rotor hub, which may be the rotatable tubular shaft if the blades are directly attached to the inner tubular shaft, like a multiblade propeller. The blade may also be characterized by a pitch angle, which can define an angle of a distal or proximal face of the blade 252 to a reference line extending radially from the rotatable tubular shaft and perpendicular to the axis A. In one example, the blade can be twisted to provide a generally constant pitch radially from root to tip. Pitch of the blade 252 converts torque of the rotatable tubular shaft to axial fluid thrust in the channel 290 by deflecting or accelerating the fluid along the axis A.

In still another example, the rotor 250 can be formed as a void in the inner tubular shaft 218, such as via an etching into the inner tubular shaft 218. In such an example, the diameter of the rotor 250 is less than the diameter of the outer surface 284 of the inner tubular shaft 218. In this example, the helicoid blade is formed as an axially-extending canal or void in the inner tubular shaft 218, which radially extends the depth of the channel 290 in the location of the rotor 250 rather than as a member extending into the channel 290.

During operation of the system, fluid is forced (via gravity or a debrider system pump applied to the fluid source) into the channel 290 in from the proximal end region 210 axially towards the distal end region 212. The rotor 250 is applied via rotation of the inner tubular shaft 218 to accelerate the fluid axially toward the distal end region 212. The distal end region 212 includes a fluid port 242 configured to discharge fluid from the device 200. In some examples, the distal end region 212 can be configured with a nozzle at the fluid port 242, or a deformable nozzle, to allow a user to specifically direct the shape of a fluid stream from the fluid port 242.

The example inner tubular shaft 216 forms a lumen 246 terminating at a suction port 244 on the distal end 280. The lumen 246 may be placed in fluid communication with a source of suction, such as suction source 136, via the handpiece 106 and suction connector 140 in FIG. 1 to selectively apply suction at the distal end 212, such as via controls on the handpiece or the IPC.

Figure 3:
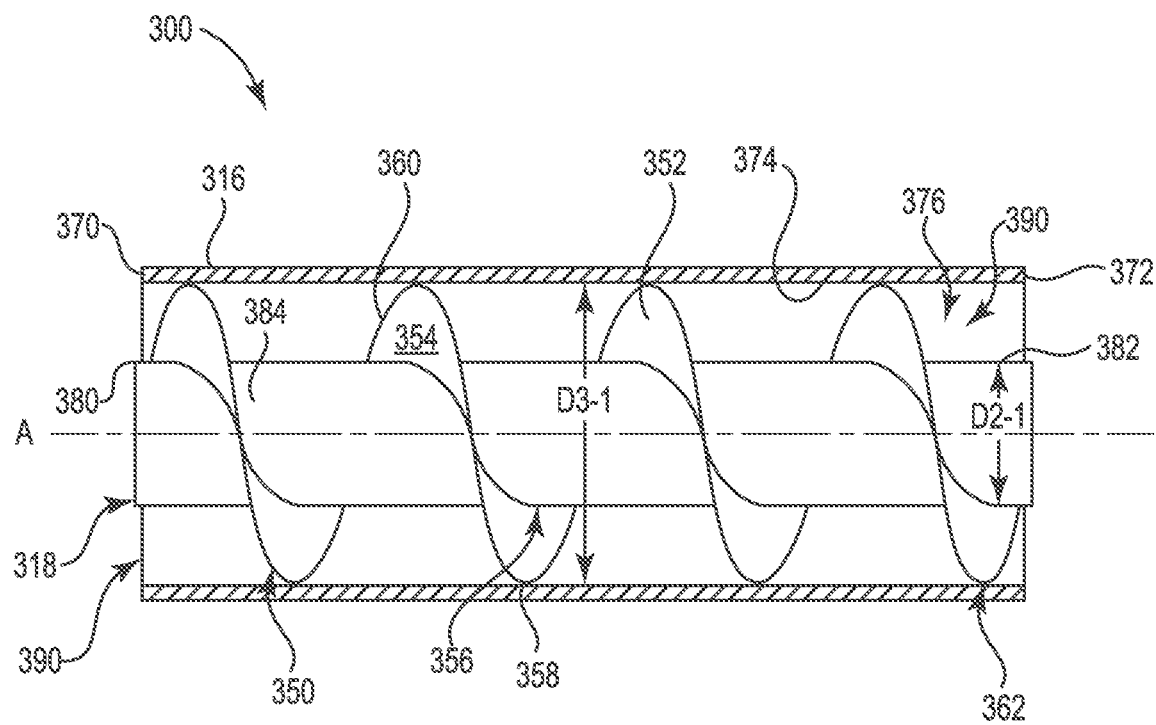
FIG. 3 is a schematic partially-sectioned side view of an example device having an example inner tubular shaft having a rotor that may be used in an example rotatable debridement device of the debridement system of FIG. 1.
Figure 4:
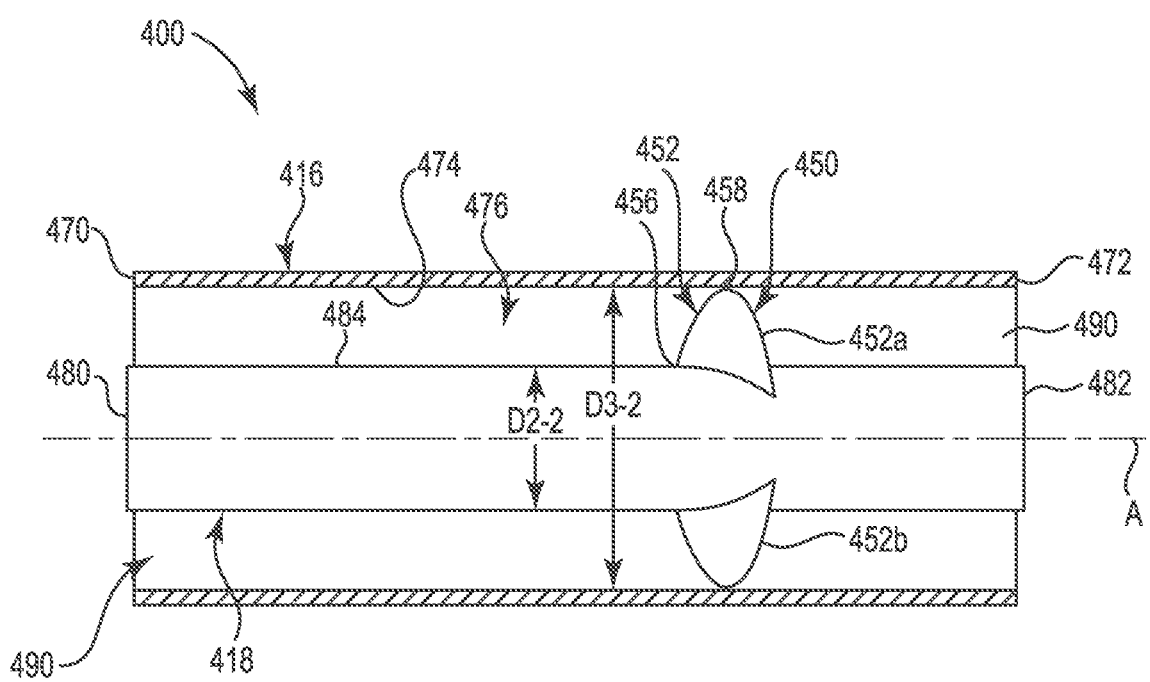
FIG. 4 is a schematic partially-sectioned side view of an example device having another example inner tubular shaft having a rotor that may be used in an example rotatable debridement device of the debridement system of FIG. 1.

FIGS. 3 and 4 illustrate examples of devices having inner tubular shafts, such as inner tubular shafts 118, 218, having a rotor, such as rotor 150 that may be used in an example rotatable debridement device 106 of the debridement system 100 of FIG. 1. The configuration of the inner tubular shafts with rotors of the examples are presented for illustration, and other configurations of a rotor having an axially extending helicoid blade coupled to the inner tubular shaft in which the helicoid blade rotates within and with respect to an outer tubular shaft and exerts an axial thrust on fluid in the channel with respect to the outer tubular shaft are contemplated as within the scope of the disclosure. Other examples may be utilized and structural or logical changes may be made without departing from the scope of the present disclosure. Further, features of the various examples described herein may be combined, in part or whole, with each other. For example, an inner tubular shaft may include multiple rotors, such as a plurality of rotors disposed on the inner tubular shaft and axially spaced-apart from each other on an outer surface of the inner tubular shaft. Changes made be made to features of the blade, such as to the configuration of the root, tip, pitch, axial length, or, for example in the case of blades radially space-apart from each other around a circumference of the inner tubular shaft (like a multiblade propeller), the number of blades around the circumference. Additionally, the helicoid blades are illustrated as extending radially from the inner tubular shafts, but may be constructed as recesses, sub-channels, or canals formed into the inner tubular shafts that, while rotating with fluid in the channel, exert an axial thrust on the fluid in the channel with respect to the outer tubular shaft. Still further, the rotors may be formed from helicoid blades radially extending from the inner tubular shaft and recessed into the inner tubular shaft that, while rotating with fluid in the channel, exert an axial thrust on the fluid in the channel with respect to the outer tubular shaft. The rotors and helicoid blades are schematically illustrated in FIGS. 3 and 4.

FIG. 3 is an example device 300 including inner tubular shaft 318 having a rotor 350 that may be used in an example rotatable debridement device 106 of the debridement system 100 of FIG. 1. The device 300 may be included with an outer tubular shaft, such as outer tubular shaft 316 having a distal end 370, a proximal end 372, an inner surface 374 defining a lumen 376. Inner tubular shaft 318 includes a distal end 380, a proximal end 382, and an outer surface 384 that include an outer surface diameter D2-1 that is less than the inner surface diameter of a companion outer tubular shaft 316. The inner surface 374 of the companion outer tubular shaft is spaced-apart from the outer surface 384 of the inner tubular shaft 318. The inner surface 374 of the companion outer tubular shaft 316, together with the outer surface 384 of the inner tubular shaft 318, form a channel 390 along the axis A, and the channel 390 is configured to receive fluid from the fluid source, such as fluid source 134.

The rotor 350 includes an axially extending helicoid blade 352 coupled to the inner tubular shaft 318, the helicoid blade to rotate within and with respect to the outer tubular shaft and exert an axial thrust on the fluid in the channel with respect to the outer tubular shaft. The helicoid blade 352 includes a face 354 extending radially from root 356 to tip 358. In the example, the diameter D3-1 of the blade 352, or rotor 350, at the tip 358 is selected to be about equal to or less than the inner surface diameter of the outer tubular shaft. In the illustrated example, the helicoid blade 352 extends axially for greater than one revolution. For instance, the helicoid blade 352 is wrapped around the inner tubular shaft 318 for greater than one helicoid revolution, or around more than one circumference of the inner tubular shaft 318 such as in an Archimedes screw. In one example, the blade can include a constant pitch. In the illustrated example, however, the blade 352 includes a variable pitch. For example, the rate of revolution of the blade 352 is greater at the proximal end of the blade 362 than the distal end of the blade 362 (i.e., the axial length of the revolution of the rotor is less for a greater rate of revolution).

FIG. 4 is an example device 400 including inner shaft 418 having a rotor 450 that may be used in an example rotatable debridement device 106 of the debridement system 100 of FIG. 1. The device 400 may be included with an outer tubular shaft, such as outer tubular shaft 416 having a distal end 470, a proximal end 472, an inner surface 474 defining a lumen 376. Inner tubular shaft 418 includes a distal end 480, a proximal end 482, and an outer surface 484 that include an outer surface diameter D2-2 that is less than the inner surface diameter of a companion outer tubular shaft 416. The inner surface 474 of the companion outer tubular 416 shaft is spaced-apart from the outer surface 484 of the inner tubular shaft 418. The inner surface 474 of the companion outer tubular shaft 416, together with the outer surface 484 of the inner tubular shaft 418, form a channel 490 along the axis A, and the channel 490 is configured to receive fluid from the fluid source, such as fluid source 134.

The rotor 450 includes an axially extending helicoid blade 452 coupled to the inner tubular shaft 418, the helicoid blade to rotate within and with respect to the outer tubular shaft and exert an axial thrust on the fluid in the channel with respect to the outer tubular shaft. The helicoid blade 452 includes a face extending radially from root 456 to tip 458. In the example, the diameter D3-2 of the blade 452, or rotor 450, at the tip 458 is selected to be about equal to or less than the inner surface diameter of the outer tubular shaft. In the illustrated example, the helicoid blade 452 includes a plurality of helicoid blades, such as blade 452a and blade 452b. In this example, the plurality of helicoid blades 452 are radially spaced-apart around the circumference of the rotor hub of the rotor 450 or, if the blades are attached or formed from the inner tubular shaft 418, the inner tubular shaft 418. Each of the helicoid blades 452 extend axially for less than one revolution. For instance, the helicoid blade 452 is wrapped around the inner tubular shaft 418 for less than one helicoid revolution. The helicoid blades 452 rotate within and with respect to the outer tubular shaft 116 and exert an axial thrust on the fluid in the channel 190 with respect to the outer tubular shaft 116.

Although the present disclosure has been described with reference to preferred embodiments, workers skilled in the art will recognize that changes can be made in form and detail without departing from the spirit and scope of the present disclosure.

What is claimed is:

1. A debridement system, comprising:
   a handpiece operatively coupled to and driven by a power console and coupled to a source of fluid to receive the fluid, and
   an irrigation device coupled to the handpiece to receive the fluid, the irrigation device including a distal end and proximal end along an axis, the irrigation device comprising:
      an outer tubular shaft, and having an inner surface having an inner surface diameter and defining a lumen along the axis;
      an inner tubular shaft rotatable within the outer tubular shaft, the inner tubular shaft having an outer surface having an outer surface diameter less than the inner surface diameter forming a channel along the axis, the channel configured to receive a fluid from the fluid source; and
      a rotor having an axially extending helicoid blade coupled to the inner tubular shaft, the helicoid blade to rotate within and with respect to the outer tubular shaft and exert an axial thrust on the fluid in the channel with respect to the outer tubular shaft.

2. The debridement system of claim 1 wherein the handpiece includes a proximal end and a distal end, and wherein the power console is operably coupled to the proximal end of the handpiece and the irrigation device is coupled to the distal end of the handpiece.

3. The debridement system of claim 2 wherein the inner tubular shaft is operably coupled to and rotated by the power console.

4. The debridement system of claim 2 wherein the irrigation device is removably coupled to the handpiece.

5. The debridement system of claim 4 and further comprising a blade or bur, wherein the irrigation device is interchangeable with the blade or bur.

6. The debridement device of claim 2 wherein the power console provides fluid to the handpiece via a fluid connector, and fluid is provided to the channel of the irrigation device from the handpiece.

7. The debridement device of claim 1 and further comprising a pump to supply fluid from the source of fluid to the handpiece.

8. The debridement device of claim 1 and further comprising a suction source operably coupled to the handpiece, wherein the inner tubular shaft of the irrigation device defines an inner lumen along the axis, and the suction source is in fluid communication with the inner lumen.

9. A device for use with a debrider system and coupleable to a fluid source, the device comprising:
- an outer tubular shaft including a distal end and proximal end, and having an inner surface having an inner surface diameter and defining a lumen along an axis;
- an inner tubular shaft rotatable within the outer tubular shaft, the inner tubular shaft having an outer surface having an outer surface diameter less than the inner surface diameter forming a channel along the axis, the channel configured to receive a fluid from the fluid source; and
- a rotor having an axially extending helicoid blade coupled to the inner tubular shaft, the helicoid blade to rotate within and with respect to the outer tubular shaft and exert an axial thrust on the fluid in the channel with respect to the outer tubular shaft.

10. The device of claim 9 wherein the debrider system includes a handpiece and wherein the proximal end is configured to be releasably coupled to the debrider system.

11. The device of claim 9 wherein the debrider system includes a handpiece and wherein the inner tubular shaft includes a proximal end region configured to be rotated by the handpiece.

12. The device of claim 9 wherein the distal end includes a nozzle.

13. The device of claim 9 wherein the helicoid blade is one of integrally formed with the inner tubular shaft or includes a spline attached to the inner tubular shaft.

14. The device of claim 9 wherein rotor includes a rotor diameter equal to the inner surface diameter of the outer tubular shaft.

15. The device of claim 9 wherein the rotor includes a hub forming a hub lumen, and the helicoid blade is coupled to the hub.

16. The device of claim 9 wherein the helicoid blade includes a constant pitch.

17. The device of claim 9 wherein the helicoid blade includes a variable pitch.

18. The device of claim 9 wherein the helicoid blade includes a single helicoid blade.

19. The device of claim 18 wherein the single helicoid blade extends axially along the rotor for more than a one helicoid revolution.

20. The device of claim 9 wherein the helicoid blade includes a plurality of helicoid blades radially spaced-apart a circumference of the rotor, wherein each of helicoid blade of the plurality of helicoid blades extends for less than one helicoid revolution.

* * * * *